US012758300B2

(12) United States Patent
James et al.

(10) Patent No.: US 12,758,300 B2
(45) Date of Patent: Oct. 13, 2026

(54) PRESSURE RELIEF VENT FOR SURGICAL SEALING DEVICES

(71) Applicant: GYRUS ACMI, INC, Westborough, MA (US)

(72) Inventors: Ian James, Cardiff (GB); Paul Wootton, Cardiff (GB)

(73) Assignee: GYRUS ACMI, INC, Westborough, MA (US)

( * ) Notice: Subject to any disclaimer, the term of this patent is extended or adjusted under 35 U.S.C. 154(b) by 811 days.

(21) Appl. No.: 17/961,303

(22) Filed: Oct. 6, 2022

(65) Prior Publication Data

US 2023/0112208 A1 Apr. 13, 2023

Related U.S. Application Data

(60) Provisional application No. 63/254,825, filed on Oct. 12, 2021.

(51) Int. Cl.

| | |
|---|---|
| ***A61B 18/14*** | (2006.01) |
| ***A61B 17/34*** | (2006.01) |
| *A61B 18/00* | (2006.01) |

(52) U.S. Cl.

CPC ...... *A61B 18/1445* (2013.01); *A61B 17/3476* (2013.01); *A61B 2018/00404* (2013.01); (Continued)

(58) Field of Classification Search

CPC ...... A61B 18/1445; A61B 2018/00404; A61B 2018/00589; A61B 2018/0063; A61B 17/3476

See application file for complete search history.

(56) References Cited

U.S. PATENT DOCUMENTS

| | | | | |
|---|---|---|---|---|
| 8,536,687 B2 * | 9/2013 | Hata | | H01L 24/40 257/E23.101 |
| 11,224,478 B2 * | 1/2022 | Ding | | A61B 18/1445 |

(Continued)

FOREIGN PATENT DOCUMENTS

| | | |
|---|---|---|
| GB | 2559370 A | 8/2018 |
| WO | 2011/044343 A2 | 4/2011 |

OTHER PUBLICATIONS

Mar. 1, 2022 Search Report issued in British Patent Application No. 2114726.9.

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

A blood vessel puncturing means within the internal cavity of the sealing jaws of an electrosurgical instrument. A forceps type electrosurgical device provided with jaws having electrically conductive sealing plates on the inner surfaces that is used to seal a blood vessel during will usually have an inner cavity of the jaws between the jaws within which a blood vessel is received and may expand during electrosurgical sealing. To prevent a blood vessel expanding during electrosurgical sealing to a dangerous size, the inner cavity is provided with a means to puncture the blood vessel in a controlled fashion, and thereby relieve the pressure within the blood vessel. The puncturing means may comprise one or more relief vents. The relief vents may provide channels to allow pressure to be vented to the external of the jaws, thus relieving the internal pressure on the jaws during coagulation.

20 Claims, 5 Drawing Sheets

(52) U.S. Cl.
CPC ............... *A61B 2018/00589* (2013.01); *A61B 2018/0063* (2013.01)

(56) References Cited

U.S. PATENT DOCUMENTS

| | | | | |
|---|---|---|---|---|
| 2011/0077647 | A1* | 3/2011 | Ambrosius ........ | A61B 18/1477 606/50 |
| 2014/0114309 | A1* | 4/2014 | Payne ................ | A61B 18/1445 606/52 |
| 2014/0221998 | A1 | 8/2014 | Latterell | |
| 2019/0192178 | A1 | 6/2019 | Batchelor | |

* cited by examiner

PRESSURE RELIEF VENT FOR SURGICAL SEALING DEVICES

TECHNICAL FIELD

Embodiments of the present disclosure relate to a pressure release arrangement in a forceps type electrosurgical sealing device. In particular, embodiments relate to pressure relief mechanisms built into an electrosurgical sealing device for sealing blood vessels that prevent the blood vessels from bursting during an electrosurgical coagulation and sealing procedure.

BACKGROUND TO THE INVENTION AND PRIOR ART

Electrosurgical forceps type sealing and cutting devices are known in the art. One prior art example from the present Applicant is described in, for example, GB2559370A, which describes a forceps type device provided with clamping surfaces having electrodes thereon to clamp and seal a blood vessel using a RF electrosurgical signal, and then to deploy a cutting blade within a track within the sealing plates to then sever the sealed blood vessel. FIG. 1 illustrates such a forceps type electrosurgical instrument.

More particularly, within FIG. 1 an end effector shown generally at 3801 comprises an upper jaw 3802 pivotably connected to a lower jaw 3803 about a pivot 3804. Flanges 3805 are present at the proximal end of upper jaw 3802, while flanges 3806 are present at the proximal end of lower jaw 3803. The flanges 3805 & 3806 each have cam slots 3807 through which a drive pin 3808 extends, such that proximal and distal movement of the drive pin 3808 (by means of a drive mechanism (not shown) causes the jaws 3802 & 3803 to pivot between open and closed positions.

A metallic shim 9 is present on the inward face of upper jaw 3802, while a metallic shim 3810 is present on the inward face of lower jaw 3803. When the jaws 3802 & 3803 pivot into their closed position, the metallic shims 9 & 3810 come into close proximity one with the other, in order to grasp tissue (not shown) therebetween.

The upper shim 9 has a generally planar surface, with the exception of a longitudinal groove (not visible in FIG. 1) running the length thereof. The lower shim 3810 has a corresponding groove 3811, the grooves in the shims 9 & 3810 accommodating the longitudinal movement of a cutting blade (not shown).

The lower shim 3810 is also provided with a plurality of metallic stop members 3812, disposed along the length of the shim and situated on either side of the groove 3811. The stop members 3812 will now be described in more detail. Reference can be made to FIGS. 38 and 39 of GB2559370A for further details.

Each metallic stop member 3812 is constituted by the upper dome of a stop element, which is enclosed in an insulating member such that it encapsulates the stop element isolating it from the remainder of the shim 3810. Each insulating member and stop element is positioned in a corresponding aperture present within the shim 3810, such that the upper portion of the insulating member forms an insulating ring around each stop member 3812.

When the jaws 3802 & 3803 are moved to their closed position, the stop. members 3812 contact the upper shim 9 maintaining a separation between the upper and lower shims of between 80 and 200 microns. In use, coagulating electrosurgical energy is supplied between the shims 9 & 3810, and the separation of the shims ensures effective sealing of tissue grasped between the jaw members 3802 & 3803. In' the meantime, electrical shorting between the shims is prevented, as the stop members 3812 are electrically isolated such they do not carry the same electric potential as the remainder of the shim 3810. The metallic stop members 3812 are rigid, allowing for a sufficient separation of the shim surfaces to ensure electrical isolation.

FIG. 2 illustrates one problem that can occur with large jaw electrosurgical sealing devices, in that steam can build up in blood vessels during sealing, causing the blood vessel that is being sealed to burst within the jaw. Within FIG. 2 a jaw sealing device comprises upper jaw 20 and lower jaw 22. Mounted on each jaw are electrosurgical sealing plates 26*a*-*d*, with respective plates on both the upper and lower jaws in opposing relation to each other, such that when the jaws are closed the sealing plates are brought together (subject to any stops which may be included to prevent short circuiting). The blood vessel 24 is received in use between the sealing plates on the upper and lower jaws 20 and 22.

Large jaw devices can exert forces of up to 60-70N on the vessels when actuated to a latched state, as shown in FIG. 2*a*, with the red (vertically oriented) arrows indicating the direction of clamping force. As the electrosurgical waveform begins to coagulate the blood vessel, the portion of the vessel in between the electrodes is subject to heat build up, causing the vessel to expand within the internal space for the mechanical blade track. This is shown in FIG. 2*b*.

On some occasions, due to the high clamping force the pressure build up cannot escape and the vessel can 'Pop' within the blade track space within the jaws (see FIG. 2*c*). This causes fragments of vessel tissue to be displaced within the blade track which can cause problems with the cut blade deployment and retraction after completing a mechanical cut which, can cause user inconvenience. In addition, such "popping" events can also cause gas to be forced back through the clamped blood vessel, potentially damaging the seal that is formed.

On other occasions the pressure build-up is able to overcome the clamping force (see FIG. 2*d*—the red (vertically oriented) arrows show how the clamping force has been overcome and the jaws are opened by the pressure build up). The blue (horizontally oriented) arrows in FIG. 2*d* show the pressure build up escaping back through the electrodes and being expelled outward. This could possibly damage the seal that is being created during coagulation and could perhaps be the cause of post-operative bleeding in blood vessels that initially appear to have been successfully coagulated by the generator which, has indicated to the user that it has met the required end point and is therefore complete.

Addressing the issue of pressure build up within blood vessels that are being electrosurgically sealed is therefore important to improve patient safety and clinical outcomes from the electrosurgical sealing procedure.

SUMMARY OF THE INVENTION

Examples of the present disclosure are intended to address the above problem by the provision of blood vessel pressure relief means within the internal cavity of the sealing jaws of an electrosurgical instrument. In particular, a forceps type electrosurgical device provided with jaws having electrically conductive sealing plates on the inner surfaces thereof that is used to seal a blood vessel during a surgical procedure will usually have an inner cavity of the jaws between the jaws within which a blood vessel is received and may expand during electrosurgical sealing. In order to prevent a blood vessel expanding during electrosurgical sealing to a dangerous size where it might otherwise uncontrollably burst, the inner cavity is provided with a means to, for example, puncture the blood vessel in a controlled fashion, and thereby relieve the pressure within the blood vessel. The puncturing means may comprise one or more relief vents, which may be designed like hypodermic needles, which are provided in a fixed position within the internal cavity of the jaws so as to impinge upon and puncture a blood vessel that is being sealed which grows to an otherwise dangerous size within the cavity. The relief vents may provide channels through the body of the jaws so as to allow pressure to be vented to the external of the jaws, thus relieving the internal pressure on the jaws during coagulation and ensuring that the jaws remain tightly shut and achieve a good tissue seal.

In view of the above, from a first aspect the present invention provides a jaw-type end effector for an electrosurgical instrument, comprising: upper and lower jaw members provided with tissue sealing electrodes thereon, arranged in use to receive a blood vessel to be sealed, to clamp the blood vessel between the upper and lower jaw members, and to apply an RF coagulating signal thereto via the tissue sealing electrodes to seal the blood vessel, the end effector further comprising blood vessel pressure relief means positioned within the jaw members such that when the jaw members are closed about a blood vessel to be sealed the blood vessel pressure relief means relieve expansionary pressure in the blood vessel should the blood vessel expand when being sealed to a critical size that affects the efficacy of the end effector in forming a seal.

With such an arrangement the blood vessel pressure relief means acts to relieve the pressure in the blood vessel in a controlled manner should the blood vessel expand whilst being sealed. This ensures that no uncontrolled expansion and bursting of the blood vessel can occur during the coagulation and sealing process.

In one example the blood vessel pressure relief means are positioned within an interior cavity of the jaw members such that they relieve the pressure in the blood vessel if the blood vessel expands to or above a predetermined size. In another example the blood vessel pressure relief means are positioned within an interior cavity of the jaw members such that they relieve the pressure in the blood vessel prior to the blood vessel expanding to a size such that any of the following would occur: a) the end effector would not otherwise remain clamped on the blood vessel; b) the blood vessel would uncontrollably burst; or c) a defective blood vessel seal would be formed. Thus in these cases, some expansion of the blood vessel is permitted, but the blood vessel pressure relief means take action to limit the expansion if the blood vessel expands past a critical size that prevents proper working and performance of the end effector.

In one example multiple blood vessel pressure relief means are provided at different positions within an interior cavity of the jaw members. For example, in one example respective blood vessel pressure relief means are provided on both the upper and lower jaw members.

In one example the pressure relief means are hollow and provide a channel from the interior of the jaw member or members to the exterior thereof. This allows pressure from within the blood vessel to be vented to the exterior to prevent the jaws being forced open during a sealing operation.

In a further example the channel is sufficiently large to permit the egress of tissue debris from the coagulation operation from within the interior cavity of the jaw members. This helps to keep the interior volume of the jaws clear of tissue debris.

In one example the pressure relief means are solid, and the jaw members are arranged to provide a sufficiently large interior volume when closed to contain tissue debris from the coagulation operation.

In one example the pressure relief means are arranged to be deployable from within the walls of the jaw members. For example, the pressure relief means may be retractable back into the walls of the jaw members, wherein the pressure relief means are deployed when a sealing procedure is being undertaken and are then retracted once a sealing procedure is completed.

In another example the pressure relief means are fixed in place within the interior of the jaw members.

In most examples the pressure relief means comprise a blood vessel puncturing means arranged to puncture the blood vessel if the blood vessel expands to or above a predetermined size. For example, the blood vessel puncturing means may comprise one or more needle type structures, and the puncturing means may have a tissue puncturing point, operatively deployed in a position just above the plane of the sealing electrodes.

In some examples a pressure relieving channel venting from the interior of the jaws to the exterior is provided, the channel having a mesh or guard over the exterior exit thereof. In some examples the pressure relieving channel is part of the blood vessel pressure relief means.

From a further aspect there is also provided an electrosurgical instrument comprising: an end effector as described above; and a handpiece mounting the end effector and including one or more activation switches, buttons or handles to allow a user to operate the instrument to open and close the jaw members and to provide an RF electrosurgical signal to the tissue sealing electrodes.

Additionally provided is an electrosurgical system, comprising an electrosurgical instrument according to the above, and an electrosurgical generator to generate the RF coagulating signal and supply it to the electrosurgical instrument.

BRIEF DESCRIPTION OF THE DRAWINGS

Embodiments of the invention will now be further described by way of example only and with reference to the accompanying drawings, wherein like reference numerals refer to like parts, and wherein.

DETAILED DESCRIPTION OF THE EMBODIMENTS

Figure 1:
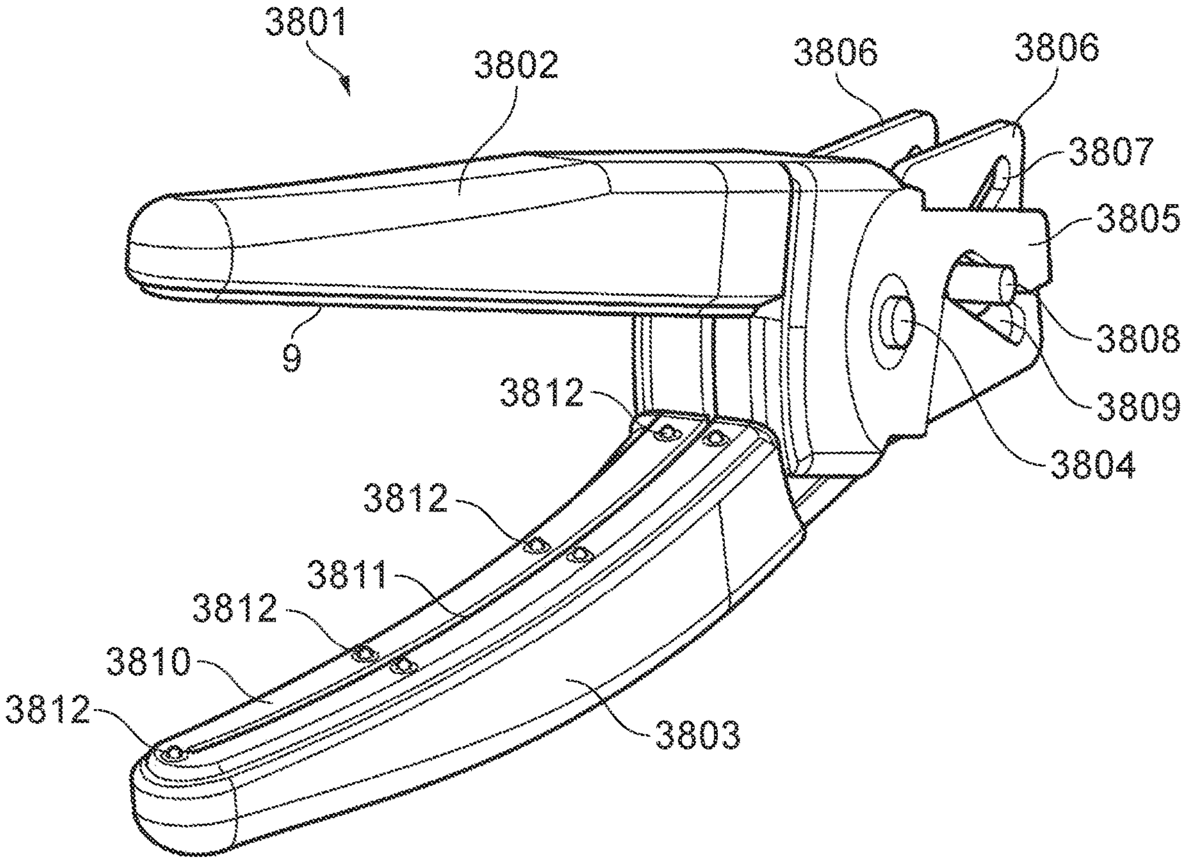
FIG. 1 is a drawing of a prior art electrosurgical sealing forceps arrangement.
Figure 2A:
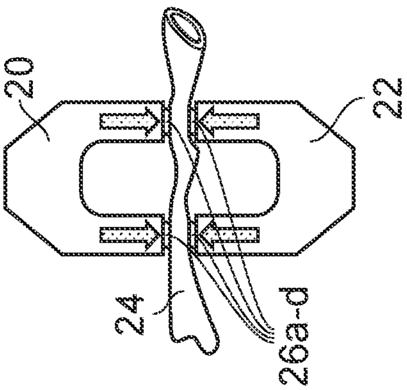
FIGS. 2*a* to 2*d* are a series of drawings illustrating how a blood vessel can burst during electrosurgical sealing in a jaw based type sealing device.
Figure 2B:
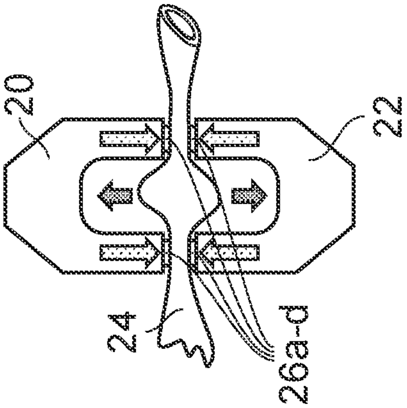
Figure 2C:
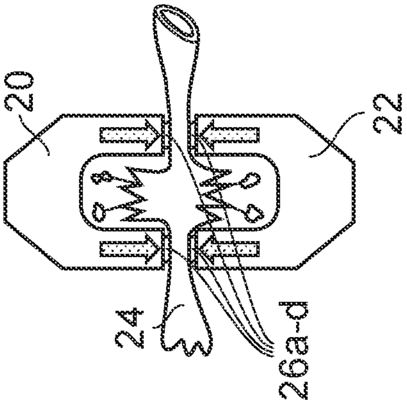
Figure 2D:
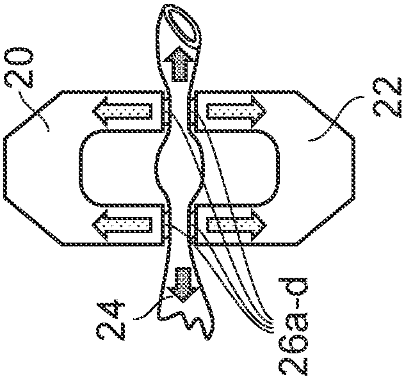

Embodiments of the present invention provide an end effector for an electrosurgical instrument in the form of a jaw-based clamping, sealing and cutting device, for example arranged as a pair of forceps. Typically embodiments of the present invention provide upper and lower jaws in opposed relation to each other, the opposing inner surfaces of the jaws being provided with electrically conductive sealing plates, which are electrically connected in use to an electrosurgical generator. In use a blood vessel to be sealed is seized and held within the jaws, and an electrosurgical coagulation signal applied to the conductive sealing plates to seal the blood vessel.

In some jaw arrangements there is an internal cavity between two sets of opposing sealing plates on the upper and lower jaws respectively. As the blood vessel is sealed between the two sets of sealing plates the part of the blood vessel within the inner cavity of the jaws can expand, in some ways in a balloon-like fashion, due to the increasing temperature and pressure caused by the RF coagulation signal heating the tissue. If the blood vessel expands excessively to the point where it uncontrollably bursts then tissue fragments can foul the electrosurgical instrument, and in addition a defective blood vessel seal can be formed, which may post-operatively bleed, with attendant deleterious consequences for the patient. In order to prevent this from occurring, a blood vessel pressure relief means is provided within the jaw cavity, positioned to relieve the pressure in the blood vessel held between the jaws should it expand to a size where it might burst. The blood vessel pressure relief means may take the form of blood vessel puncturing means, such as, for example, fixed relief vents placed on the inside of the blade track positioned just above the electrodes. Relief vents are placed above electrodes to ensure the device jaws remains atraumatic during manipulation.

During coagulation the heat/pressure build-up in the vessel will push the expanding walls of the vessel onto the relief vents. The multiple relief vents will puncture the vessel in a controlled manner, thus reducing the pressure build-up and avoiding the vessel bursting inside of the blade track. This would eliminate the build-up of coagulated vessel fragments in the blade track which, can hinder deployment/retraction of mechanical cut blade.

In addition, and as a one of the main benefits, by relieving the pressure build-up, the blood vessel pressure relief means will avoid situations whereby the pressure overcomes the jaw force and expels pressure/steam back through the portions of the vessel that are being sealed between the electrodes which, could be detrimental to seal quality without it being recognised by the generator/user. Thus, the positioning of the blood vessel puncturing means with respect to the sealing plates is such that the puncturing means operates to puncture a blood vessel as it grows in size within the clamped jaws before it reaches a size that would cause the jaw clamping force to be momentarily overcome, releasing pressure back through a newly formed seal. As noted above positioning the blood pressure puncturing means just above the sealing plates reliably achieves this, although other positions may be possible depending on the precise design of the jaws.

The fixed relief vents can be designed like hypodermic needles (i.e. are hollow), allowing the pressure to be relieved externally through the cross-section of the jaw assembly. Moreover, the relief vents can also be made to be deployable on activation of the hand/foot switch for the electrosurgical generator. Moreover, when pressure has been expelled to the outside of the jaw, evidence of the pressure relief can be seen from the outside. A surgeon is then able to see this and understand that a possible 'Popping' event may have taken place within the jaws which can lead them to make another seal downstream to be extra sure that the vessel has been securely sealed.

Alternatively, in some devices which have larger jaws, there should be enough internal capacity within internal cavity of the jaws that contains the blade track for the pressure to be relieved internally within the device jaws. In this case, the blood vessel puncturing means do not need to vent the blood vessel to the exterior of the jaws, and can instead for example be blind needles (i.e. solid, not hollow), or any other sharp shape that simply impinge against and puncture any growing blood vessel, with the contents of the blood vessel then being contained within the interior of the closed jaws.

The effect of embodiments in relieving the pressure build-up in a blood vessel that is being sealed is to enable the clamp force to remain consistent and allow the electrodes to coagulate the tissue in between without being affected by the pressure build-up.

In another embodiment one option is to have deployable relief vent(s) that are only deployed when the coagulation hand-switch/foot-switch is activated. These vents then project from the body of jaws into the interior cavity therein when the electrosurgical generator is activated, but otherwise are contained within the jaw body. Once activation has ceased, then the relief vent would return to a fully shrouded safe position. This would guarantee that the device would remain atraumatic when being used for tissue manipulation If it is possible to relieve the pressure externally, then the jaws can be provided with a vent from the interior of the jaws to the exterior to help dissipate the expulsion of pressure without causing any harm to patient or user. Such a vent may be covered with grid bars or a mesh design which can help to prevent material re-entering into the interior of the jaws, and to prevent foreign objects from blocking the vent.

Further features and benefits of embodiments of the disclosure will become apparent from the following description of embodiments thereof with respect to the Figures.

Figure 3:
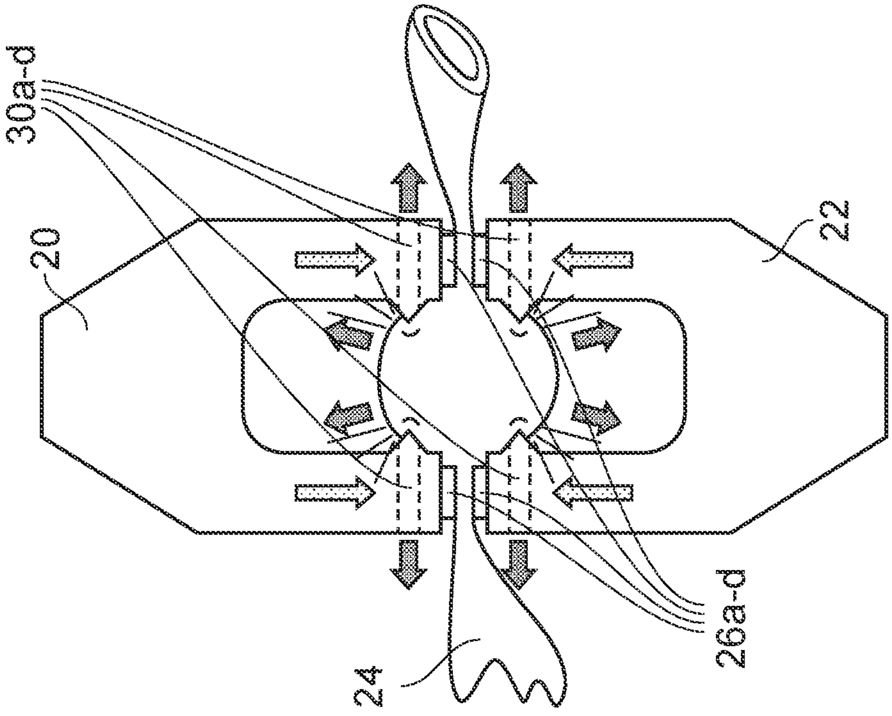
FIG. 3 is a drawing of a first embodiment of the present invention.

Turning first to FIG. 3, a jaw-based clamping and sealing device according to a first embodiment comprises an upper jaw member 20 and a lower jaw member 22. The upper jaw member 20 has formed on lower sealing surfaces thereof respective electrodes 26*a* and 26*b*. Correspondingly, the lower jaw member 22 has formed on upper sealing surfaces thereof respective electrodes 26*c* and 26*d*. The lower sealing surface of upper jaw 20 and the upper sealing surface of lower jaw 22 are in opposed relation thereto, such that the respective sealing surfaces formed thereon are also in opposing relation. Thus, when the members 20 and 22 are closed and the respective sealing surfaces brought together, blood vessel 24 placed within the jaws will be seized and clamped within the jaws, and an electrosurgical coagulating signal can then be applied to electrodes 26 in order to seal the blood vessel.

As shown in FIG. 3, when a blood vessel is being sealed the heat and resulting temperature of the blood vessel can rise, thus increasing the pressure within the vessel, and causing it to balloon upwards and downwards within the interior cavity of the jaws device. In order to prevent the ballooning blood vessel from either bursting uncontrollably or forcing the jaw members apart, blood vessel puncturing means 30*a*-30*d* are provided on the surface of the interior cavity of the jaws, located just above each of the sealing electrodes 26*a* to 26*d*. That is, in this embodiment a respective puncturing means is provided for each sealing electrode. However, in other embodiments, fewer or more puncturing means may be provided. For example, in another embodiment, only one or two puncturing means may be provided to puncture the blood vessel.

In this embodiment, the puncturing means take the form of a hypodermic needle, with a channel running therethrough from the interior of the jaws to the exterior surface thereof. This allows blood and other tissue from within the punctured blood vessel to be evacuated from within the interior of the jaws to the exterior. However, in other embodiments these channels may not be necessary, and in particular if the interior cavity of the jaws is sufficient to accept the material from within the punctured blood vessel. That is, if the interior cavity of the jaws is large enough to accept the material from within the punctured blood vessel without forcing the jaws open, then it may not be necessary to provide the channels running from the interior cavity of the jaws to the exterior.

In embodiments of the invention the puncturing means 30*a* to 30*d* may take the form of hypodermic needles with hollow channels therein, or, where it is not necessary to provide such channels, as described above, solid blind needles or other sharp devices. The puncturing means should be provided positioned within the interior cavity of the jaws just above the electrodes such that the blood vessel cannot expand to a sufficient extent to force the jaws open without impinging upon one of the puncturing means, and being punctured. The precise positioning of the puncturing means within the jaws within this constraint will depend on the size and shape of the interior cavity.

Figure 4:
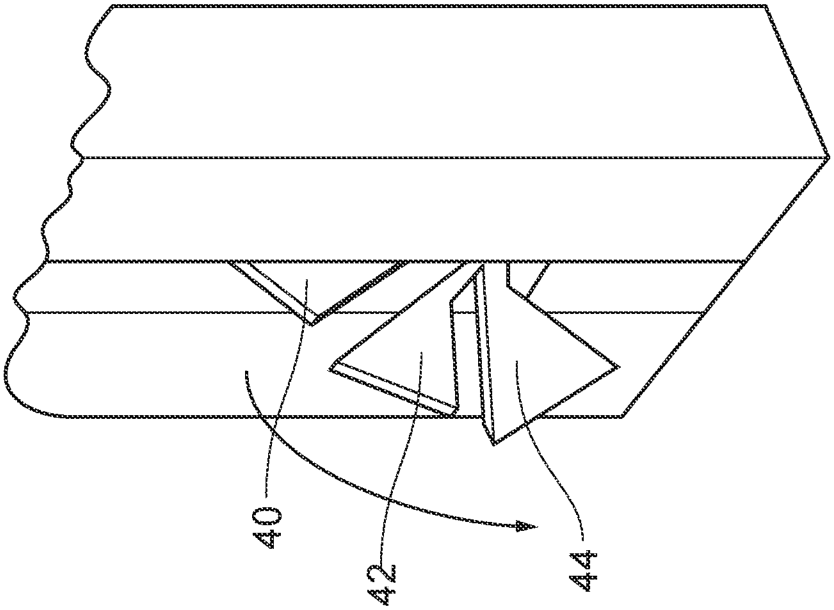
FIG. 4 is a drawing of a further embodiment of the present invention.

FIG. 4 shows an alternative arrangement for the puncturing means. Here the puncturing means comprises a sharp, triangular flag shaped member, which is rotatably mounted with a hinge (not shown) within a slot formed in the wall of the jaw members 20 and 22. When the device is unclamped the flag shaped member is retained within the slot, as shown in position 40, meaning the jaws are atraumatic. However, when required to be used to puncture a blood vessel, and the jaws are in a clamped state ready for sealing, the sharp flag shaped member is rotated so as to be deployed outwards from its slot passing through position 42, and coming to rest in position 44, as shown in FIG. 4. In a further embodiment, the sharp flag-shaped member is deployed when both the jaws are clamped shut, and the coagulation signal is being applied to the sealing electrodes. Howsoever the sharp flag-shaped member is deployed, once in the deployed position the sharp point of the triangular flag shape member is pointing downwards (in the case of the upper jaw member), such that if the blood vessel increases in size it will impinge upon the sharp point, and be punctured. It will be understood that the corresponding arrangement can be provided in the lower jaw member, where the triangular flag shaped member rotates upwards.

Figure 5:
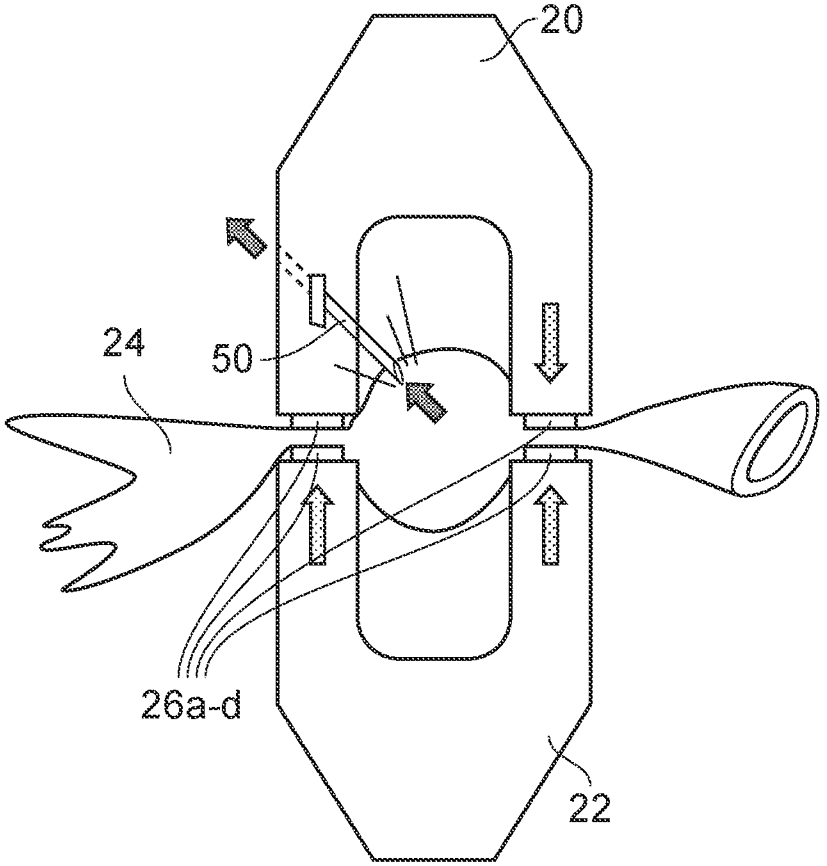
FIG. 5 is a drawing of a yet further embodiment of the present invention.
Figure 6:
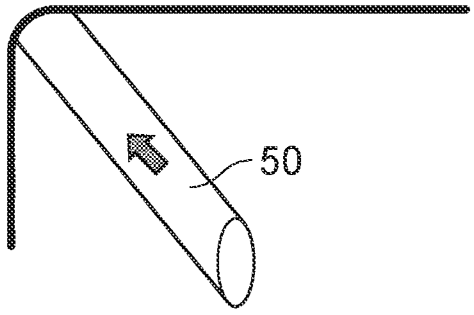
FIG. 6 is a drawing of a part of the embodiment of FIG. 5.

FIGS. 5 and 6 show a yet further alternative embodiment. Here, instead of multiple fixed puncturing means being provided, a single, retractable, puncturing means in the form of a hypodermic needle 50 is provided within the wall of the upper jaw member 20. More particularly, a hypodermic needle 50 having a channel formed therethrough is mounted within the wall of the upper jaw member 20 diagonally pointing downwards through the wall, towards the sealing plane of the jaw member where the blood vessel would normally be when clamped. When in use, the hypodermic needle 50 is deployed from within the wall of the upper jaw member 20 to a position just above the sealing electrodes 26*a* and *b*, such that if the blood vessel expands to an unwanted extent, it will impinge the point of the needle 50, and be punctured. When not required i.e. when sealing is not taking place, the hypodermic needle 50 may be retracted back into its own channel within the wall of the upper jaw member 20.

In variations of the above multiple needles 50 may be provided extending from the upper and lower jaw members, to provide multiple puncturing means in the same manner as for example in the embodiment of FIG. 3.

Figure 7:
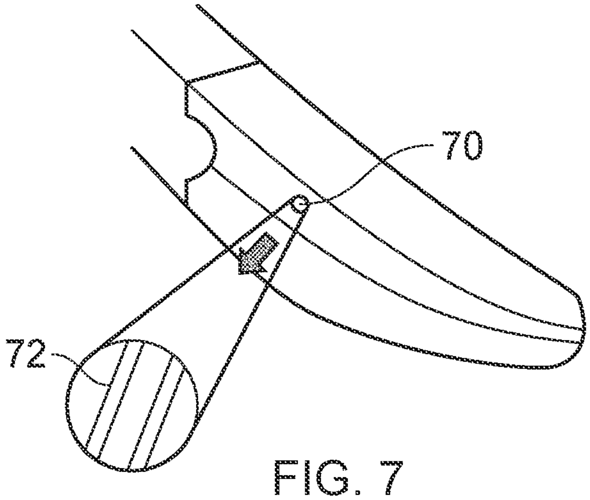
FIG. 7 is drawing of a modification that can be applied to the embodiments of the invention.

FIG. 7 shows a modification that may be applied to any of the above-described embodiments where the puncturing means are provided with vents through the walls of the jaw members. In particular, a grid mesh or bar members 72 may be provided over the outer opening 70 of any such vents to prevent the ingress of foreign material into the vents from the outside of the jaw members, and thus causing them to be blocked.

Figure 8:
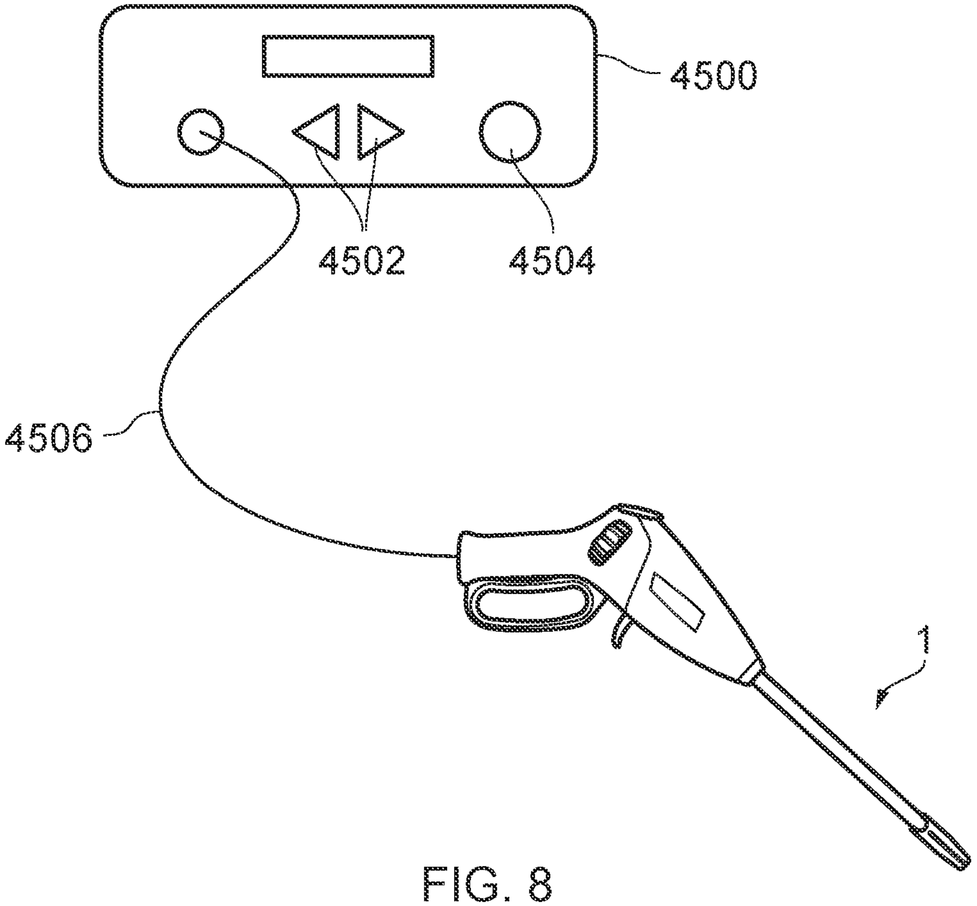
FIG. 8 is a drawing of an electrosurgical system having a forceps type electrosurgical device to which the concepts of the present invention may be applied.

FIG. 8 shows an electrosurgical system that makes use of the embodiments of the invention described herein. More particularly, electrosurgical instrument 1 having an end effector having a blood vessel puncturing means as described in the previous embodiment is connected to an electrosurgical generator 4500 having a controllable radiofrequency (RF) source therein (not shown) that in use produces RF coagulation energy that coagulates or seals tissue when applied thereto via the electrodes of the end-effector of the instrument 1. Electrosurgical generator 4500 includes control input switches 4504 and 4502, to respectively allow the generator to be turned on and off, and to allow the power of the RF coagulation energy fed to the instrument 1 to be controlled. In these respects, the electrosurgical generator 4500 is conventional.

The instrument 1 is connected in use to generator 4500 by control and power line 4506, which contains separate electrical lines to allow RF energy to be fed to the end-effector of the instrument 1 via internal wiring, and also to allow a control signal to be received from the switch of the instrument 1, to command the electrosurgical generator to output RF coagulation energy to the instrument 1. In use the surgeon activates the generator via on-off switch 4504, and selects the coagulation or sealing energy strength to be generated by the internal RF source using buttons 4502. During a surgical procedure with the instrument when sealing or coagulation RF energy is required at the end-effector, the surgeon controls the generator to produce such a signal by pressing an activation switch on the instrument or generator, or using a footswitch (not shown), the generated RF signal then being passed via the electrical lines 4506 to the end-effector. That is, activation of the generator in use causes RF coagulation or sealing energy to be supplied to the sealing plates 26*a-d* (see FIG. 3) contained within the end-effector.

If during sealing the blood vessels expand sufficiently to impinge upon the puncturing means, then the puncturing means will act to puncture the blood vessels in a controlled manner. As such, pressure is then relieved within the blood vessels and the coagulation and vessel sealing procedure can proceed as intended, with the result that a more reliable blood vessel seal is obtained.

Various further modifications to the above described embodiments, whether by way of addition, deletion or substitution, will be apparent to the skilled person to provide additional embodiments, any and all of which are intended to be encompassed by the appended claims.

The invention claimed is:

1. A jaw-type end effector for an electrosurgical instrument, comprising:

upper and lower jaw members provided with tissue sealing electrodes thereon, arranged in use to receive a blood vessel to be sealed, to clamp the blood vessel between the upper and lower jaw members, and to apply an RF coagulating signal thereto via the tissue sealing electrodes to seal the blood vessel; and a blood vessel pressure relief member positioned within an interior cavity of the upper and lower jaw members such that when the upper and lower jaw members are closed about a blood vessel to be sealed the blood vessel pressure relief member relieves expansionary pressure in the blood vessel responsive to the blood vessel expanding when being sealed to or above a predetermined size that affects an efficacy of the jaw-type end effector in forming a seal, wherein:

the blood vessel pressure relief member comprises a plurality of blood vessel puncturing members arranged to puncture the blood vessel when the blood vessel expands to or above the predetermined size;

the plurality of blood vessel puncturing members comprises at least one pair of blood vessel puncturing members including a first blood vessel puncturing member provided at a first interior surface of one of the upper and lower jaw members and a second blood vessel puncturing member provided at a second interior surface of the one of the upper and lower jaw members; and the second interior surface is located opposite the first interior surface such that the first blood vessel puncturing member and the second blood vessel puncturing member face each other across the interior cavity of the upper and lower jaw members.

2. The jaw-type end effector according to claim 1, wherein each member of the plurality of blood vessel puncturing members is positioned within the interior cavity of the upper and lower jaw members such that each member relieves pressure in the blood vessel prior to the blood vessel expanding to a size such that any of the following would occur:

a) the jaw-type end effector would not otherwise remain clamped on the blood vessel;

b) the blood vessel would uncontrollably burst; or c) a defective blood vessel seal would be formed.

3. The jaw-type end effector according to claim 1, wherein multiple blood vessel pressure relief members are provided at different positions within the interior cavity of the upper and lower jaw members.

4. The jaw-type end effector according to claim 1, wherein respective blood vessel pressure relief members are provided on both the upper and lower jaw members.

5. The jaw-type end effector according to claim 1, wherein the blood vessel pressure relief member is hollow and provides a channel from the interior cavity of at least one of the upper jaw member or the lower jaw member to an exterior thereof.

6. The jaw-type end effector according to claim 5, wherein the channel is sufficiently large to permit an egress of tissue debris from a coagulation operation from within the interior cavity of the upper and lower jaw members.

7. The jaw-type end effector according to claim 1, wherein the blood vessel pressure relief member is solid, and the upper and lower jaw members are arranged to provide a sufficiently large interior volume when closed to contain tissue debris from a coagulation operation.

8. The jaw-type end effector according to claim 1, wherein the plurality of blood vessel puncturing members are arranged to be deployable from within a wall of the upper jaw member and a wall of the lower jaw member.

9. The jaw-type end effector according to claim 8, wherein the plurality of blood vessel puncturing members are retractable back into the walls of the upper and lower jaw members, wherein the plurality of blood vessel puncturing members are deployed when a sealing procedure is being undertaken and are then retracted once the sealing procedure is completed.

10. The jaw-type end effector according to claim 1, wherein the plurality of blood vessel puncturing members are fixed in place within the interior cavity of the upper and lower jaw members.

11. The jaw-type end effector according to claim 1, wherein the plurality of blood vessel puncturing members comprise one or more needle type structures.

12. The jaw-type end effector according to claim 1, wherein each member of the plurality of blood vessel puncturing members includes a tissue puncturing point, operatively deployed in a position just above a plane of the tissue sealing electrodes.

13. The jaw-type end effector according to claim 1, further comprising:

a pressure relieving channel venting from the interior cavity of the upper and lower jaw members to an exterior, the pressure relieving channel having a mesh or guard over an exterior exit thereof.

14. The jaw-type end effector according to claim 13, wherein the pressure relieving channel is part of the blood vessel pressure relief member.

15. The jaw-type end effector according to claim 1, wherein each member of the plurality of blood vessel puncturing members is a structure including a sharp edge configured to pierce the blood vessel.

16. The jaw-type end effector according to claim 1, wherein each member of the plurality of blood vessel puncturing members is a needle or a sharp device.

17. The jaw-type end effector according to claim 1, wherein each member of the plurality of blood vessel puncturing members is positioned parallel to the tissue sealing electrodes and perpendicular relative to a longitudinal axis of the electrosurgical instrument.

18. An electrosurgical instrument comprising:

a jaw-type end effector, comprising an upper jaw member and a lower jaw member provided with tissue sealing electrodes thereon, arranged in use to receive a blood vessel to be sealed, to clamp the blood vessel between the upper jaw member and the lower jaw member, and to apply an RF coagulating signal thereto via the tissue sealing electrodes to seal the blood vessel;

a blood vessel pressure relief member positioned within an interior cavity of the upper jaw member and the lower jaw member such that when the upper jaw member and the lower jaw member are closed about a blood vessel to be sealed the blood vessel pressure relief member relieves expansionary pressure in the blood vessel responsive to the blood vessel expanding when being sealed to or above a predetermined size that affects an efficacy of the jaw-type end effector in forming a seal, wherein the blood vessel pressure relief member comprises a plurality of blood vessel puncturing members arranged to puncture the blood vessel when the blood vessel expands to or above the predetermined size, wherein:

the plurality of blood vessel puncturing members comprises at least one pair of blood vessel puncturing members including a first blood vessel puncturing 2 member provided at a first interior surface of one of the upper jaw member or the lower jaw member and a second blood vessel puncturing member provided at a second interior surface of the one of the upper jaw member or the lower jaw member; and the second interior surface is located opposite the first interior surface such that the first blood vessel puncturing member and the second blood vessel puncturing member face each other across the interior cavity of the upper jaw member and the lower jaw member; and a handpiece mounting the jaw-type end effector and including one or more activation switches, buttons or handles to allow a user to operate the electrosurgical instrument to open and close the upper jaw member and the lower jaw member and to provide an RF electrosurgical signal to the tissue sealing electrodes.

19. The electrosurgical instrument according to claim 18, wherein the electrosurgical instrument is included in an electrosurgical system comprising:

an electrosurgical generator to generate the RF coagulating signal and supply the RF coagulating signal to the electrosurgical instrument.

20. A jaw-type end effector for an electrosurgical instrument, comprising:

upper and lower jaw members provided with tissue sealing electrodes thereon, arranged in use to receive a blood vessel to be sealed, to clamp the blood vessel between the upper and lower jaw members, and to apply an RF coagulating signal thereto via the tissue sealing electrodes to seal the blood vessel; and a blood vessel pressure relief member positioned within an interior cavity of the upper and lower jaw members such that when the upper and lower jaw members are closed about a blood vessel to be sealed the blood vessel pressure relief member relieves expansionary pressure in the blood vessel responsive to the blood vessel expanding when being sealed to or above a predetermined size that affects an efficacy of the jaw-type end effector in forming a seal, wherein:

the blood vessel pressure relief member comprises a blood vessel puncturing member arranged to puncture the blood vessel when the blood vessel expands to or above the predetermined size; and the blood vessel puncturing member is arranged parallel to the tissue sealing electrodes.

* * * * *